(12) United States Patent
Hunter et al.

(10) Patent No.: US 6,763,699 B1
(45) Date of Patent: Jul. 20, 2004

(54) GAS SENSORS USING SIC SEMICONDUCTORS AND METHOD OF FABRICATION THEREOF

(75) Inventors: Gary W. Hunter, Oberlin, OH (US); Philip G. Neudeck, Ohmsted Falls, OH (US)

(73) Assignee: The United States of America as represented by the Administrator of Natural Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/359,940

(22) Filed: Feb. 6, 2003

(51) Int. Cl.[7] ............................................. G01M 7/04
(52) U.S. Cl. ..................................... 73/31.06; 73/31.05
(58) Field of Search ............................. 73/31.05, 31.06

(56) References Cited

U.S. PATENT DOCUMENTS

| | | | |
|---|---|---|---|
| 4,126,532 A | 11/1978 | Takao et al. | |
| 4,343,768 A | * 8/1982 | Kimura | 422/97 |
| 4,457,161 A | 7/1984 | Iwanaga et al. | 73/31.05 |
| 4,928,513 A | 5/1990 | Sugihara et al. | |
| 5,248,385 A | 9/1993 | Powell | |
| 5,618,496 A | 4/1997 | Hasumi et al. | |
| 5,698,771 A | 12/1997 | Shields et al. | 73/31.05 |
| 5,915,194 A | 6/1999 | Powell et al. | 438/478 |
| 6,027,954 A | 2/2000 | Hunter | 438/49 |
| 6,109,094 A | 8/2000 | Baranzahi et al. | 73/31.06 |
| 6,161,421 A | 12/2000 | Fang et al. | 73/31.05 |
| 6,165,874 A | 12/2000 | Powell et al. | 438/478 |
| 6,291,838 B1 | 9/2001 | Hunter | 259/76 |
| 6,297,138 B1 | 10/2001 | Rimai et al. | 438/597 |
| 6,298,710 B1 | * 10/2001 | Samman et al. | 73/31.06 |
| 6,378,355 B2 | 4/2002 | Samman et al. | 73/31.06 |
| 6,461,944 B2 | 10/2002 | Neudeck et al. | 438/478 |
| 6,488,771 B1 | 12/2002 | Powell et al. | 117/89 |
| 2001/0015170 A1 | 8/2001 | Kitabatake et al. | 117/95 |
| 2001/0032493 A1 | 10/2001 | Samman et al. | 73/31.06 |
| 2002/0019117 A1 | 2/2002 | Nagasawa | |
| 2002/0020853 A1 | 2/2002 | Nakashima et al. | |

OTHER PUBLICATIONS

Hunter, G. W. et al., "SiC–Based Gas Sensor Development", NASA Technical Memorandum 2000–209653, prepared for International Conference on Silicon Carbide and Related Materials Oct. 10–15, 1999, Jan. 2000, pp. 1–5.*

Hunter, G. W. et al., "SiC–Based Schottky Diode Gas Sensors", NASA Technical Memorandum 113159, prepared for International Conference on SiC and Related Materials Aug. 31–Sep. 15, 1997, Oct. 1997, pp. 1–5.*

Uehara, K. et al., "AIN Epitaxial Film With Atomically Flat Surface for GHz–Band Saw Devices", 2002, IEEE Ultrasonics Symposium, 2002, pp. 135–138.*

G. W. Hunter et al "State–of–the–Art Program on Compound Semiconductor for Photonic and Electronic Devices and Sensors III" Given at the Spring 2002 Meeting or the Electrochemical Society, Philadelphia PA, 2002.

G. W. Hunter et al "Silicon Carbide, III—Nitrides and Related Materials" Published in the Proceeding of International Conference on SiC and Related Material, Stockholm, Sweden, Sep. 1997.

(List continued on next page.)

*Primary Examiner*—Daniel S. Larkin
(74) *Attorney, Agent, or Firm*—Kent N. Stone; John P McMahon (57) ABSTRACT

Gas sensor devices are provided having an atomically flat silicon carbide top surface that, in turn, provides for a uniform, and reproducible surface thereof.

33 Claims, 10 Drawing Sheets

OTHER PUBLICATIONS

G. W. Hunter et al "Silicon Carbide and Related Materials—1999" Given in the Proceedings Internatioanl Conference on Silicon Carbide and Related Materials, Oct. 10–15, 1999, Research Triangle Park, MD USA.

P. G. Neudeck "Enlargement of Step–Free SiC Surfaces by Homoepitaxial Web Growth of Thin SiC Cantilevers" Published in the Journal of Applied Physics, vol. 92, No. 5 pp 2391–2400, 2002.

H. Wingbrant et al "MISiCFET Chemical Sensors for Applications in Exhaust Gases and Flue Gases" Given in Proc. ECSCRM 2002, Linköping, Sep. 2–5, 2002.

L. Chen et al "Comparison of Interfacial and Electronic Properties of Annealed Pd/SiC and Pd/SiO2/SiC Schottky Diode Sensor" J Vac Sci Technol, A15(3), May/Jun. 1997 p. 1228.

G. W. Hunter et al "Microfabricated Chemical Sensors for Aerospace Applications" given in the CRC Handbook on MEMS, Chapter 22 Published in the CRC Press, 2001.

* cited by examiner

GAS SENSORS USING SIC SEMICONDUCTORS AND METHOD OF FABRICATION THEREOF

ORIGIN OF THE INVENTION

The invention described herein was made by employees of the United States Government and may be used by or for the Government for governmental purposes without payment of any royalties thereon or therefor.

FIELD OF THE INVENTION

The invention relates to gas sensors and methods of fabrication thereof that use a silicon carbide (SiC) substrate containing an atomically flat surface so as to produce gas sensors having improved operational characteristics including stability, reproducibility, and sensitivity.

BACKGROUND OF THE INVENTION

Silicon carbide (SiC) based gas sensors that have been produced thus far have inherent limitations regarding their stability, reproducibility, sensitivity, and electronic capabilities. An important factor affecting these limitations includes the starting SiC semiconductor material on which the gas sensors are fabricated. The standard SiC semiconductor has non-idealities which affect the circuits which can be produced on the semiconductor. The standard SiC semiconductor surface also has a stepped structure due to off-axis surface orientation that supports standard SiC homoepitaxial growth, typically 3–8 degrees off of the (0001) crystallographic basal plane. The sides, or risers, of the steps have a higher bond density and are more chemically reactive than the tops, or terraces, of the steps which detrimentally cause a varying surface structure on which electronic devices are fabricated. The varying surface, in turn, produces interface defects believed to degrade the performance of the gas sensors.

For gas sensors, such as Schottky diodes, capacitors, and Metal-Oxide-Silicon-Field-Effect-Transistors (MOSFETS), the surface properties of the interface strongly determine the response of the sensor. The non-ideal surface of off-axis SiC is believed to contribute to limitations in the quality of the oxides grown on SiC and thus the quality of the MOSFET devices. The presence of the many interface states in SiC has, for example, resulted in limitation in the quality of the oxides grown on SiC and thus the quality and performance of the SiC MOSFET device. From our efforts, it has been found that the reproducibility problems in Schottky diode devices created from conventional SiC wafers have hindered development in SiC-based gas sensor devices. Variations in semiconductor surface quality are likely a cause of these reproducibility problems associated with Schottky diodes. Pinning, that is where interface trap charge dominates the electrical properties of the surface of the semiconductor, often results in a less sensitive gas sensor. We believe that pinning may be related to the non-flat microscopic structure of the standard SiC surface. It is desired that a more uniform, step-free surface on which the SiC gas sensors are deposited be provided, which is believed to be a significant step forward in producing higher quality SiC based gas sensors.

OBJECTS OF THE INVENTION

It is a primary object of the present invention to provide silicon carbide (SiC) gas sensors having a SiC substrate with an atomically flat surface so as to reduce or even eliminate the performance degradations caused by poor SiC surface interface properties.

It is another object of the present invention to provide an atomically flat SiC substrate so as to produce a uniform, reproducible surface that improves the reproducibility of a gas sensing device.

It is another object of the present invention to provide gas sensors with an atomically flat substrate so as to reduce the reactivity otherwise previously normally occurring during the formation of steps on the interface between oxide layers making up the gas sensors, which contributes to the degradation of the gas sensors, and particularly, to the stability and sensitivity thereof.

Further still, it is an object of the present invention to provide gas sensors, such as Schottky diodes, capacitors, and MOSFETS, all having improved performance characteristics.

SUMMARY OF THE INVENTION

The present invention is directed to gas sensors, such as Schottky diodes, capacitors, metal-semiconductor diodes, metal-semiconductor field effect transistors, and MOSFETS and methods of fabrication thereof, all of which employ a silicon carbide substrate having an atomically flat surface, which is of primary importance to the present invention and provides for improvements in the stability, reproducibility, sensitivity, and electronic capability of the gas sensing device itself.

In one embodiment, a gas sensing device is provided that produces a change in electrical signal due to the presence of a gas, wherein the gas sensing device is comprised of a gas sensing layer residing on top of a single crystal silicon carbide (SiC) epilayer having an atomically flat surface.

In another embodiment, a gas sensing device is provided that produces a change in electrical signal due to the presence of a gas, wherein the gas sensing device is comprised of a gas sensing layer residing on top of an interface layer residing on top of a single crystal silicon carbide (SiC) epilayer having an atomically flat surface.

BRIEF DESCRIPTION OF THE DRAWINGS

FIG. 2 illustrates one embodiment of the present invention and is comprised of FIGS. 2A and 2B, wherein FIG. 2A is a cross-sectional view schematic drawing that illustrates atomic-scale growth steps that are produced on top of a mesa when the polished growth surface is tilted off-axis by an angle θ relative to the basal plane, and wherein

DETAILED DESCRIPTION OF THE PREFERRED EMBODIMENTS

The present invention uses an atomically flat SiC substrate to produce improved gas sensors. The atomically flat SiC substrate provides a uniform, reproducible step-free basal plane surface, which allows improved reproducibility of gas sensing devices. Overall, given improved starting material, that is, the atomically flat SiC substrate, the performance of SiC gas sensors are expected to be significantly improved by the practice of the method of the present invention using atomically flat SiC substrate.

As will be further described hereinafter, the present invention uses mesas for the formation of the atomically flat surface that has a number of advantages for gas or chemical sensor applications. The mesas themselves can serve as a controlled structure on which the chemical sensor can be deposited. The mesas can also help prevent an adjoining area from affecting the sensor response by better isolating the sensor structure. For example, Si from SiC making up the substrate of the device is believed to migrate two dimensionally from the surrounding SiC substrate to effectively disrupt the sensor structure and significantly decrease sensor response in a Pd/SiC type Schottky diode. This migration on gas sensor structures without mesa structure is described in the technical article of Liangyu Chen, G. W. Hunter & Philip G. Neudeck; "Comparison Of Interfacia And Electronic Properties Of Annealed Pd/SiC And Pd/SiO2/SiC Schottky Diode Sensors", J. Vac Sci. Technol. A 15(3), May/June 1997 p. 1228. In the mesa arrangement of one embodiment of the present invention, the sensor is on top of an isolated mesa. This mesa structure would have only allowed interaction from below the sensor, and not from the large surrounding area that occurred for the sensor described in the Chen et, al. technical article.

A second example is that there is a significant difference between the response of a Pd/SnO2/SiC diode dependent upon whether the SnO2 is only under the Pd or completely surround the Pd. This difference is described in the technical article of G. W. Hunter, P. G. Neudeck, M. Gray, D. Androjna, L. Y. Chen, R. W. Hoffman Jr., C. C. Liu, and Q. H. Wu, Silicon Carbide and Related Materials—1999, Proceedings International Conference on Silicon Carbide and Related Materials, 10–15 Oct., 1999, Research Triangle Park, Md., Calvin H. Carter, Jr., Robert P. Devaty, and Gregory S. Rohrer Eds., 1439 (1999). For gas and chemical sensors, a mesa can be formed to accommodate the type of structure necessary to optimize sensor response. In both the first and second examples, if the surface inhomogenieties exist, the results obtained by a mesa are uncertain. It is the combination, provided by this invention, of the mesa structure with atomically flat surfaces that produces better sensor performance.

A third example is that chemical sensors are often produced on diaphragm structures to minimize the thermal mass and allow minimal power consumption and quick thermal equilibrium times as described in the technical article of G. W. Hunter, C. C. Liu, and D. B. Makel, CRC Handbook on MEMS, Chapter 22, Microfabricated Chemical Sensors for Aerospace Applications, CRC Press, 2001. The present invention provides a diaphragm or cantilever structure that advantageously allows deposition of a gas sensor on a cantilever formed as part of the fabrication of an atomically flat surface yielding an innovative use of that structure for a purpose other than originally intended.

Overall, the present invention uses atomically flat SiC material which enables a multitude of gas sensor systems attempted, but not previously entirely successfully completed because of previous attempts being plagued with imperfect surface material. These include diodes, capacitors, and MESFET and MOSFET structures, known in the art, with a variety of useful advantages which are enabled by silicon carbide's high temperature electronic capabilities, but not optimized due in part to the relatively poor surface properties of typical SiC surfaces compared to silicon surfaces. This includes the advantageous formation of a sensor array composed of different sensor materials on SiC substrates, but such arrays have been inhibited by the SiC semiconductor material and structural issues associated with the sensor-SiC interfaces. Examples of this inhibition are described in the technical article of G. W. Hunter, P. G. Neudeck, L. Y. Chen, D. Knight, C. C. Liu, and Q. H. Wu, Silicon Carbide, III-Nitrides and Related Materials, Proceedings of International Conference on SiC and Related Materials, Stockholm, Sweden, Sept., 1997, G. Pensl, and H. Morkoc, B. Monemar, and E. Janzen Eds., 1093, (1998). The present invention should overcome many of these inhibitions and drawbacks, especially those related to SiC interface structure and provides improved diodes, capacitors, field effect transistors (FETs), such as MESFETs and MOSFETs, as well as other semiconductor devices.

The atomically flat SiC substrates may be fabricated in accordance to the principles described in U.S. Pat. No. 5,915,194, in particular, to the discussion given therein with reference to FIGS. 3, 5, and 6. The disclosure of U.S. Pat. No. 5,915,194, herein referred to as the '194 patent is herein incorporated by reference. Although the subject matter of the '194 patent is incorporated herein, certain portions of the disclosure are repeated herein for the sake of completeness.

As more fully described in the '194 patent, a fundamental principle regarding the formation of atomically flat SiC to serve as a substrate is the formation of mesas on the SiC substrate and the growth of epitaxial layers on these mesas. The "stepflow" epitaxial growth takes place at the step risers on the SiC substrate that occur due the tilt angle of the polished substrate surface relative to the (0001) basal plane. If growth is limited entirely to step risers on mesas that do not have step-sources, an atomically flat surface is produced.

In one embodiment, the present invention provides a gas sensing device that produces a change in electrical signal due to the presence of a gas, wherein the gas sensing device is comprised of a gas sensing layer residing on top of a single crystal silicon carbide (SiC) epilayer having an atomically flat surface.

In another embodiment, a gas sensing device is provided that produces a change in electrical signal due to the presence of a gas, wherein the gas sensing device is comprised of a gas sensing layer residing on top of an interface layer which, in turn, is residing on top of a single crystal silicon carbide (SiC) epilayer having an atomically flat surface.

Figure 1:
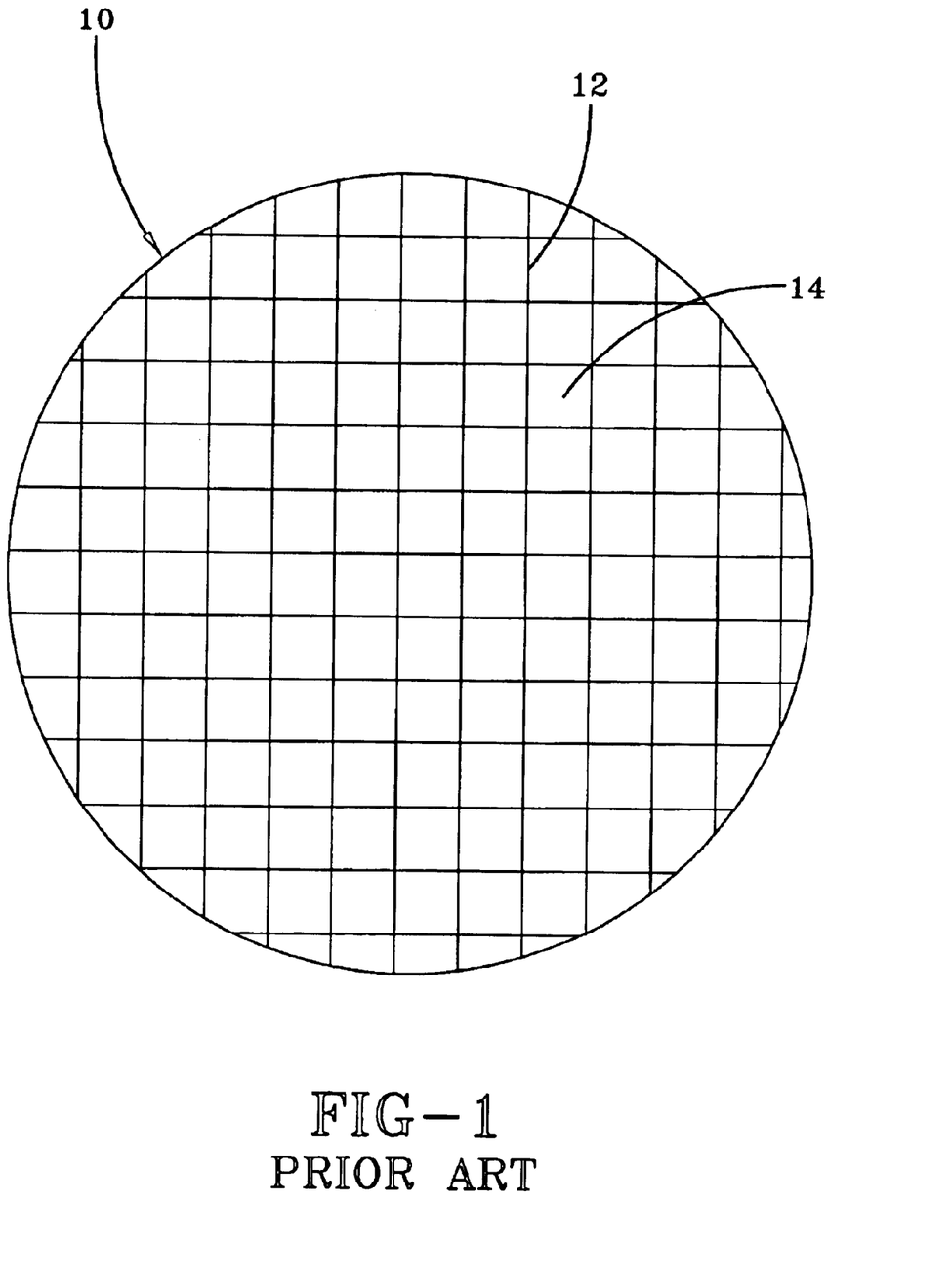
FIG. 1 is a plan view of a substrate that has been divided into isolated growth regions (mesas).

Referring now to the drawings, wherein the same reference number indicates the same element throughout, there is shown in FIG. 1 a plan view of a substrate 10, that is used in the formation as an atomically flat surface. The term "atomically flat" is defined in U.S. Pat. Nos. '194 and 6,165,874 and is generally referred to herein, as meaning a surface that is totally without any atomic-scale or micro-scale steps over an area defined by selected boundaries that may be created by grooves in a manner to be further described hereinafter.

The substrate 10 is further prepared by creating boundaries or grooves 12 on the face of the substrate 10, which form growth regions 14 (also called mesas), as illustrated in FIG. 1. The trenches 12 forming growth region boundaries that comprise mesas 14 are preferably cut by physical means, such as photolithography, laser etching, ion etching and/or photochemical or electrochemical etching processes; trenches 12 may be formed by other physical means; such as cutting with a precision dicing saw with a twenty-five micrometer thin blade to minimize crystal damage. The width of the trenches 12 need only be a few micrometers, but larger widths can also be used. The depth of the trenches 12 is preferably a few micrometers, but may be deeper or shallower. After the trenches 12 forming mesas 14 are formed in a substrate 10, the substrate receives further processing as more fully described in the '194 patent with reference to FIG. 4 therein.

Figure 2A:
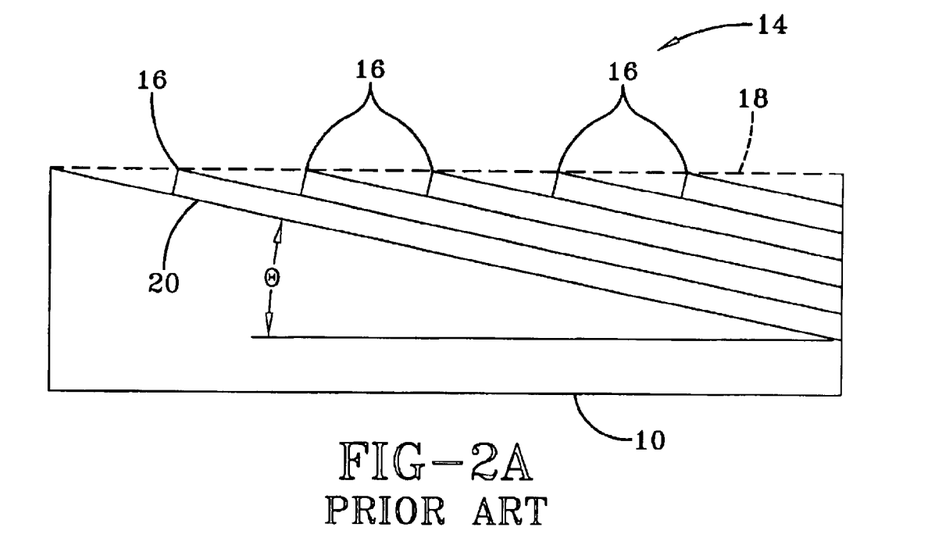

After the substrate has been pretreated in accordance to the teachings of the '194 patent, the first phase of crystal growth can be described herein by referring now to FIG. 2A where there is shown an atomic-scale cross-sectional drawing of 6H—SiC substrate mesa 14 prior to the start of growth of an interface layer to be further described hereinafter. FIG. 2A illustrates atomic-scale steps 16 that are present on the growth surface because of the tilt angle, $\theta$ of the actual growth surface 18 (shown in phantom) relative to the crystal basal plane 20. In the first phase of the growth process (to produce an atomically flat surface), growth conditions are set to promote step-flow growth, and to minimize growth by two-dimensional nucleation. These conditions consist of higher growth temperatures (1400 to 2200° C.) and lower concentrations of silane and propane. Growth of the first phase is continued until an atomically flat, or nearly atomically flat epitaxial surface is obtained and may be further described with reference to FIG. 2B.

Figure 2B:
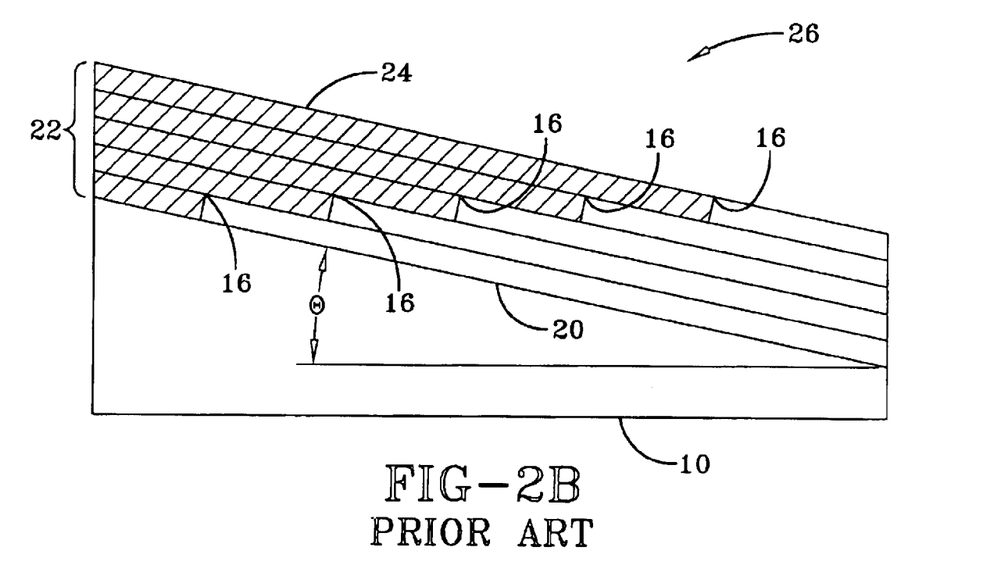
FIG. 2B is a schematic diagram illustrating an atomically-flat surface on top of a mesa achieved after homoepitaxial step-growth without two-dimensional 2D nucleation of a 6H—SiC film on a 6H—SiC substrate (under growth conditions that suppress 2D nucleation).

With reference to FIG. 2B, there is shown an atomic-scale cross-sectional drawing of a 6H—SiC substrate mesa after homoepitaxial step-flow growth (without 2D nucleation) has produced an epitaxial film 22 with an atomically flat surface 24. Typically, SiC epilayer growth rates from a carrier gas containing 200 ppm silane and 600 ppm propane produce a vertical epilayer film growth rate parallel to the c-axis of about three micrometers per hour. At this vertical rate of growth, the lateral growth of steps is much higher and is inversely proportional to the tilt angle $\theta$. The lateral growth rate for a 0.2 tilt angle and a three micrometer per hour vertical growth rate is 0.9 millimeters per hour; hence, at this rate, anatomically-flat epilayer can be grown over a 1 millimeter×1 millimeter square region in seventy minutes. This time can be reduced by using smaller tilt angles and/or smaller mesa top surface areas and/or growth conditions that produce higher growth rates. After the atomically flat surface 24 is formed, an atomically-flat substrate mesa 26 of FIG. 2B is provided for the continuation of the practice of the present invention. It should be noted that this approach is not limited to 6H—SiC or the growth conditions discussed above.

The atomically-flat silicon carbide (SiC) substrate mesa 26 has an upper surface and lower surface with the upper surface being the atomically-flat surface 24 that is embodiment of FIG. 2, the crystal basal plane 20. As described in the '194 patent, the atomically-flat surface 24 is produced on the top of mesas etched into a SiC wafer prior to growth. The silicon carbide mesa 26 having the atomically-flat surface 24 is used to provide various embodiments of the present invention one of which may be described with reference to FIG. 3. The prior art process of the '194 patent produces a wedge-shaped epilayer of non-uniform thickness as illustrated in FIG. 2B.

More particularly, the 194 process produces a wedge-shaped epilayer on top of a SiC mesa etched into a SiC substrate. However, it is important to note that this does not necessarily imply that all atomically flat SiC epilayers must have wedge-shape thickness. For example, the '194 process could be applied to a relatively thick (compared to the wedge thickness) previously grown SiC epilayer residing on top of an SiC substrate. Processes for growing the relatively thick homoepitaxial layers on the surface of "on-axis" SiC wafers are disclosed in U.S. Pat. No. 5,248,385. In contrast to the '194 process, the '385 process does not isolate growth regions from screw dislocations that provide new growth steps that supports homoepitaxial film growth in the c-axis crystallographic direction. Therefore, the '385 process enables an SiC homoepitaxial layer of desired thickness to be grown on "on-axis". Once the relatively thick SiC epilayer has been realized using the '385 process, the epilayer surface could then serve as the first selected growth surface of the '194 process. Mesas could then be etched and rendered atomically flat by further epitaxial growth under the '194 process. This would yield films of relatively uniform thickness instead of wedge-shape thickness, similar to epitaxial films illustrated in FIGS. 3, 4, 5, 8, and 9 to be further described.

Figure 3:
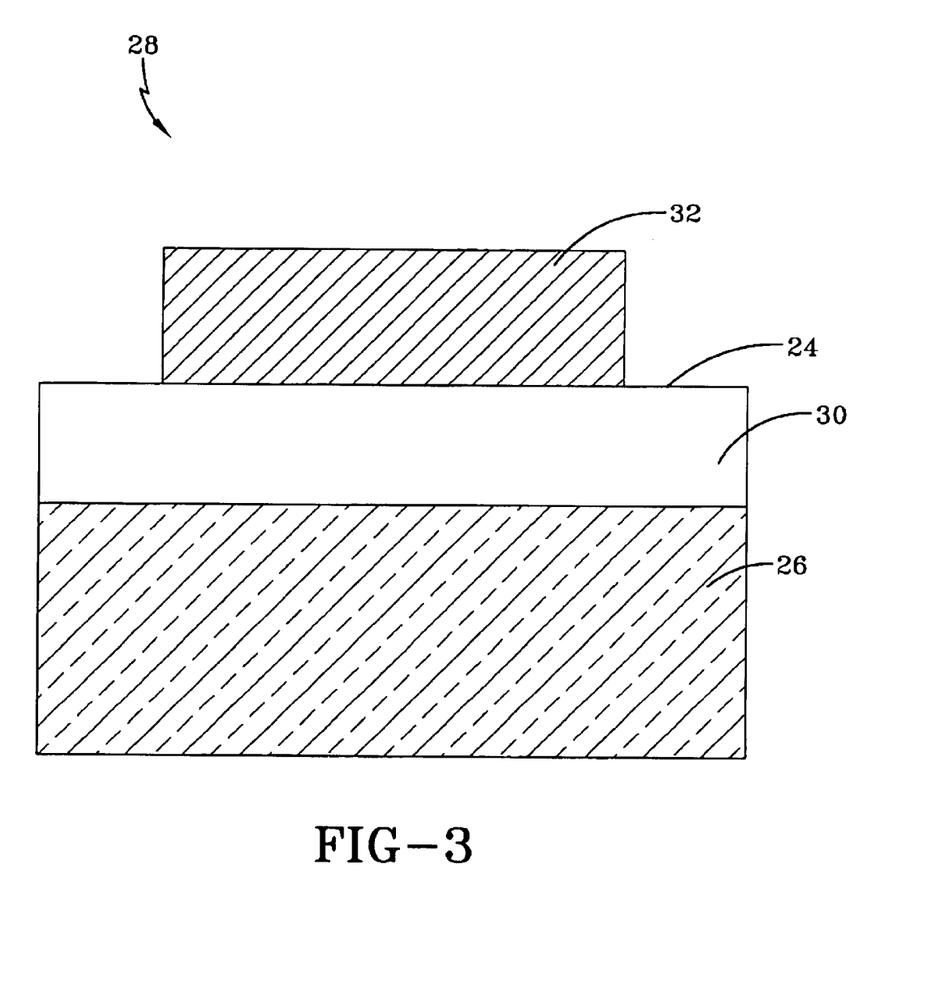
FIG. 3 illustrates a gas sensing device in accordance with one embodiment of the present invention.

FIG. 3, as well as the other embodiments of the present invention illustrated in FIGS. 4–10, for the sake of clarity, illustrate the atomically flat epilayer 30 as being relatively uniform thickness, rather than the wedge-shaped thickness of FIG. 2B. A gas sensing layer 32 is then deposited on top of the atomically flat epilayer 30. The gas sensing layer 30 is a material selected from the group consisting of Pt,Pd, Au,Ir,Ag,Ru,Rh, In,Os,Cr,Ti, and alloys of these materials with each other. The gas sensing layer 32 may also consist of oxides of materials selected from the group consisting of Sn,Ti,W,Ga, Zr,Ta, and SrTiO$_2$. In a manner known in the art, the selection of the material determines the type of gas sensor device provided by the invention. For example, the selection of the percentages of the materials Pd and Cr improved the response of a Schottky diode gas sensor made of Pd and Cr on top of SiC. The gas sensing device 28 of FIG. 3 forms the essential elements of a metal-semiconductor diode 34, sometimes referred to as a Schottky diode. Another embodiment of a gas-sensitive Scottky diode with interconnects and protective covering may further described with reference to FIG. 4.

Figure 4:
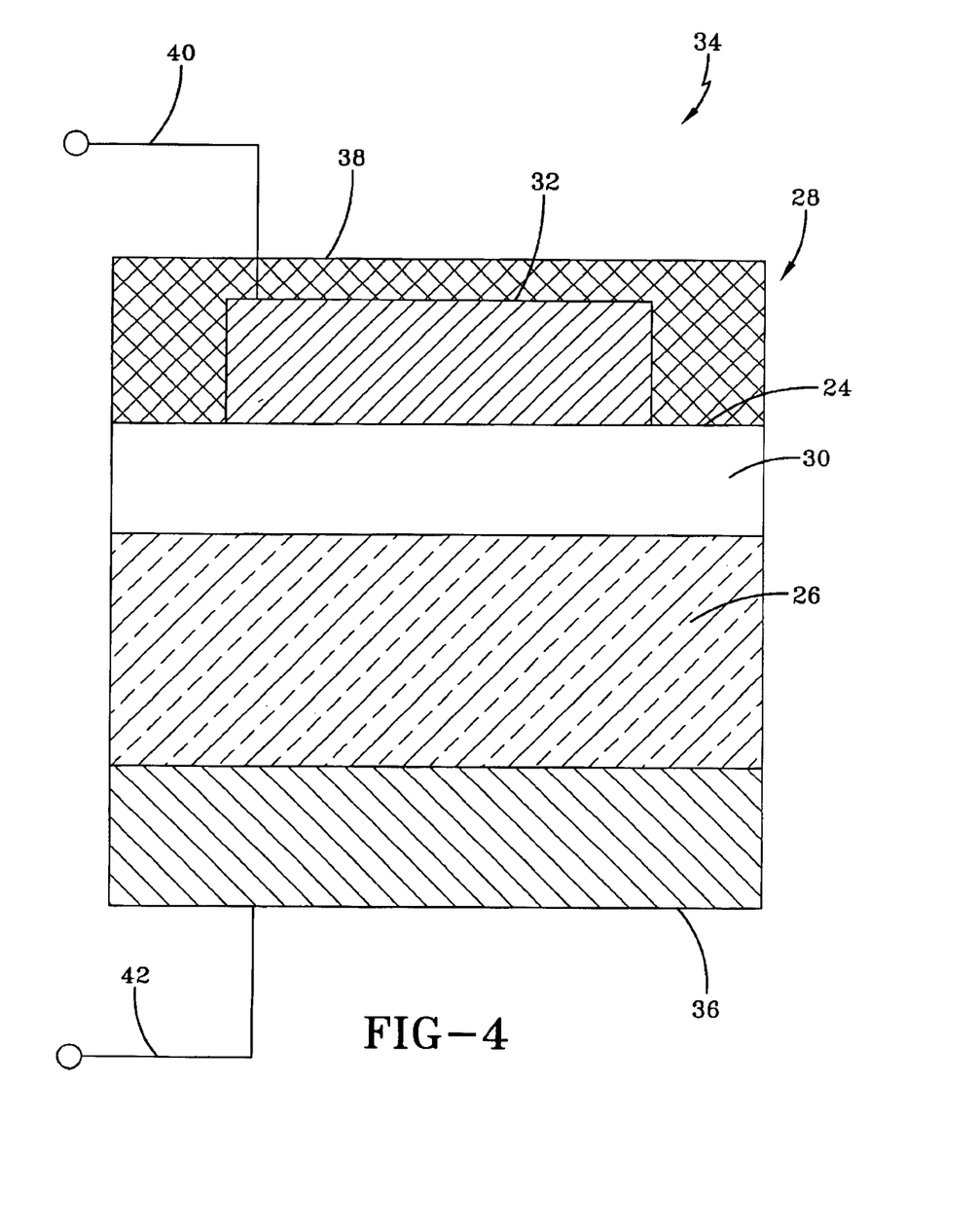
FIG. 4 illustrates a gas sensing device comprising a metal-semiconductor diode.

The metal-semiconductor diode 34 further comprises a backside contact 36, which may, be comprised of nickel or aluminum or other metal or alloy that can form an ohmic contact. Further, the metal-semiconductor diode 34 preferably further comprises a protective covering 38 comprising a filter made of high temperature material that covers the metal-semiconductor diode 34. Protective covering 38 may be of a material, such as SiO2 or other oxide. The metal-semiconductor diode 34 may be provided with electrical interconnect contacts 40 and 42, which provide an output signal produced by the metal-semiconductor diode 34. The patterning and deposition of suitable electrical interconnects is well known in the art. The electrical response of the metal-semiconductor diode 34 is determined, in a manner known in the art, by measuring the current flow of the diode at a selected applied bias. Similarly, the electrical response of the metal-semiconductor diode 34 may be determined, in a manner known in the art, by measuring the capacitance of the metal-semiconductor diode at a selected applied bias. A further embodiment of a gas sensing device 44 may be further described with reference to FIG. 5.

Figure 5:
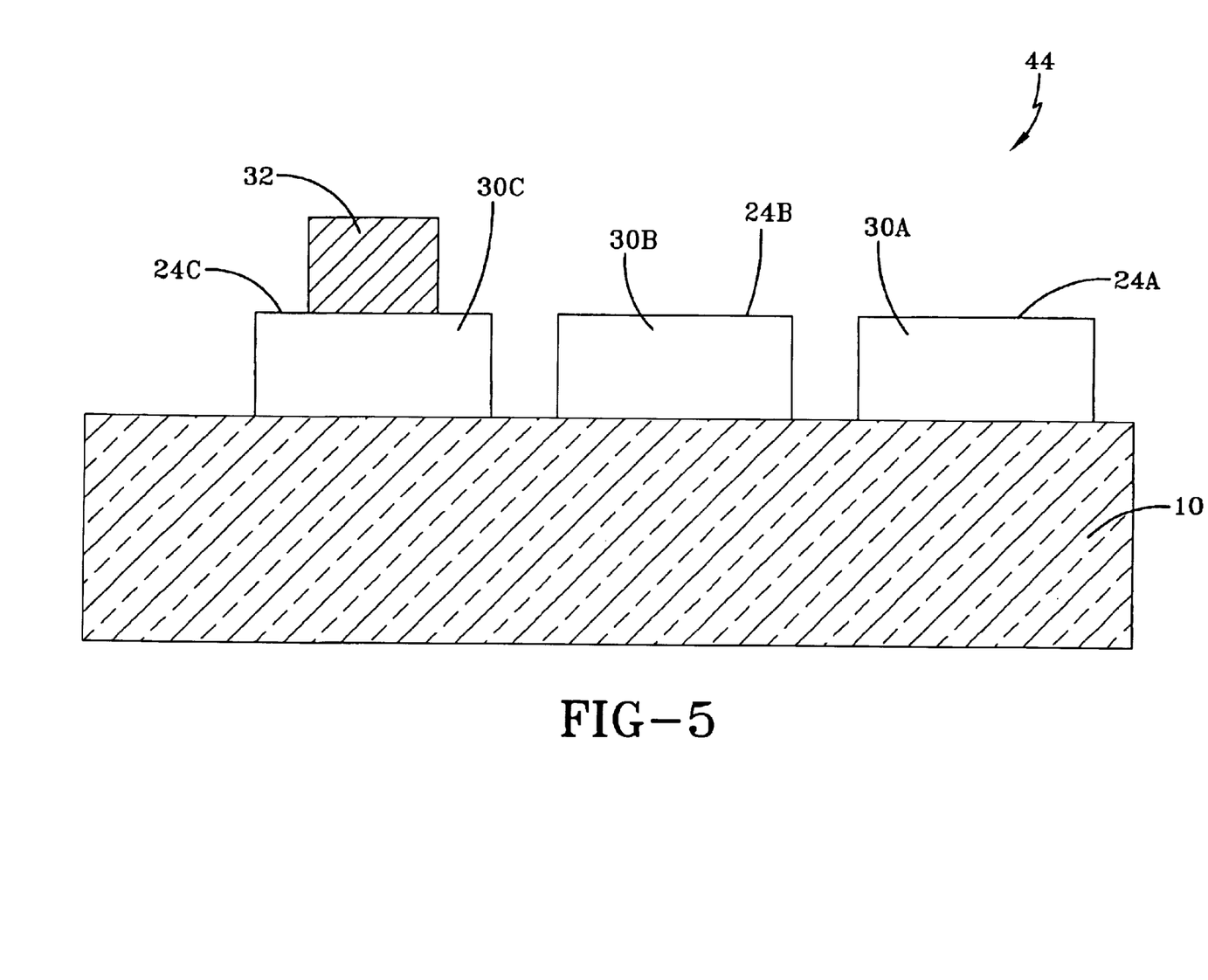
FIG. 5 illustrates a further embodiment of a gas sensing device of the present invention that uses multiple mesas patterned on a SiC substrate.

FIG. 5 illustrates the gas sensing device 44 as having the epilayer 30A, 30B, and 30C each with an atomically-flat surface 24A, 24B and 24C, that is formed on mesas patterned on the SiC substrate 10. More particularly, as seen in FIG. 5, the mesa pattern on the substrate 10 has three atomically-flat surface portions 24A, 24B, and 24C, which reside on the top of epilayer portions 30A, 30B, and 30C.

The gas sensing layer 32 resides on the epilayer portion 30C. The patterned mesas of FIG. 5 are selected so that each mesa is isolated from the other by a depth of a predetermined etch, thereby reducing or perhaps even eliminating the need for passivation surrounding the gas sensing device on epilayer portion 30C.

In one embodiment, the gas sensing selected layer 32 is incorporated onto an atomically flat mesa selected so as to form a metal-semiconductor field effect transistor in a manner known in the art. In such an embodiment, the electrical signal response of the metal-semiconductor field effect transistor is determined, in a manner known in the art, by measuring the current flow of the metal-semiconductor field effect transistor at a selected applied bias. For such applications, the current flow is usually measured at the drain electrode of the metal-semiconductor field effect transistor.

The metal-semiconductor field effect transistor, commonly referred to by acronym as MESFET, is a three-terminal transistor device well known to those skilled in the art. The MESFET is well known to have operational electrodes referred to in the art as source, drain, and gate. It is well known in the art that a MESFET has a conducting channel between the source and drain electrodes, and that the amount of current that flows through the channel when a voltage is applied between the source and drain electrodes is modulated by the depletion effect created by the gate electrode. In particular, it is well known in the art that the gate electrode in a MESFET forms a rectifying Schottky contact to the channel region that with varying gate potential depletes some or all of the electrons or holes in the channel that carries current between the source and drain. Thus, the electrical properties of the Schottky (rectifying metal semiconductor) diode formed by the gate-to-channel diode affect the amount of current flowing in a MESFET structure. Therefore, if gas sensing functionality can be performed by a simple Schottky diode structure, electronic gas sensing functionality can also be performed by a MESFET structure. Conventional MESFET-based sensor structures will suffer from the drawback that the Schottky gate contact gas-sensitive element of the structure when it is realized or implemented on a conventional "off-axis" epilayer surface with numerous steps. Therefore, the conventional MESFET devices suffer from the increased reactivity and decreased reproducibility associated with off-axis SiC interfaces with stepped surface structure. By using on-axis SiC epilayers and making the top surface of the MESFET channel atomically-flat, the gate diode metal/semiconductor interface is expected to improve in a similar manner as Schottky diode based gas sensors using an atomically-flat interface should improve. A further embodiment of the present invention may be further described with reference to FIG. 6 illustrating a gas sensing device 46.

Figure 6:
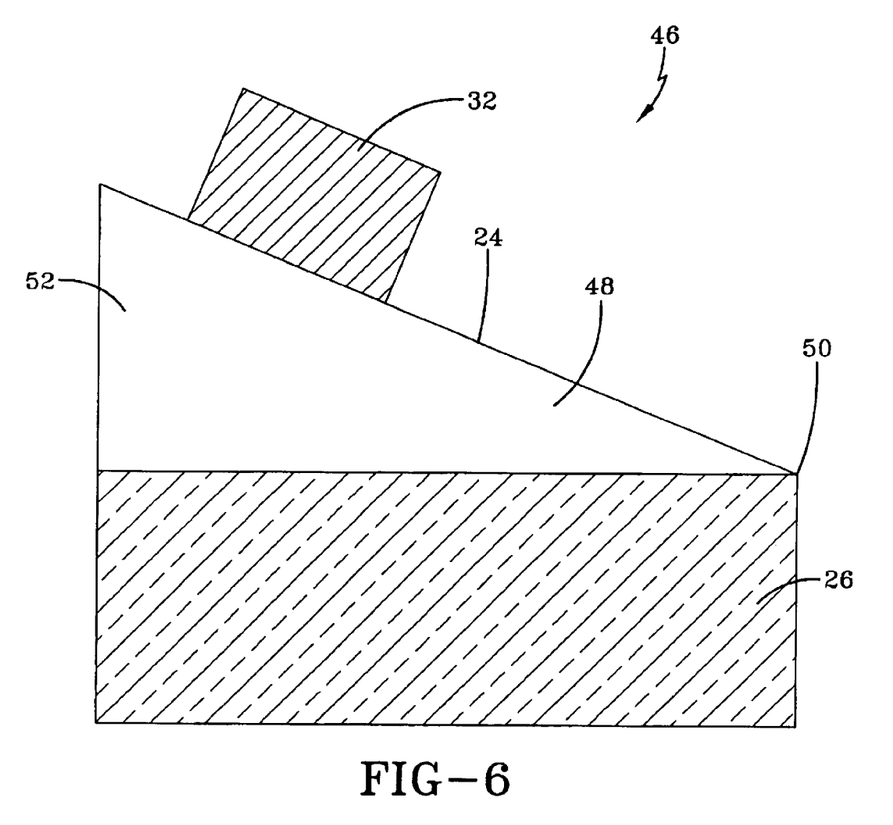
FIG. 6 is another embodiment of the present invention that uses a wedge-like epitaxial layer having a non-uniform thickness.

FIG. 6 illustrates the gas sensing device 46 as having a SiC epilayer 48, which is of a wedge-like type with non-uniform thickness, with a thickness of the epilayer 48 being essentially zero at one location 50 on the mesa formed by the atomically flat surface 24. The wedge-like layer may be formed by the processes described in U.S. Pat. No. '194, as illustrated in FIG. 2B of the present application. Further, the gas sensing device 46 preferably has the gas sensing layer 32 deposited and patterned to reside near the thickest part 52 of the wedge-like epilayer 48. This better facilitates control of the sensor properties because the electrically active depletion region can be confined to the epilayer 48, and not extend beyond the atomically flat surface. It is well known in the art that epilayers have better controlled electrical properties. A further embodiment of a gas sensing device 54 may be further described with reference to FIG. 7.

Figure 7:
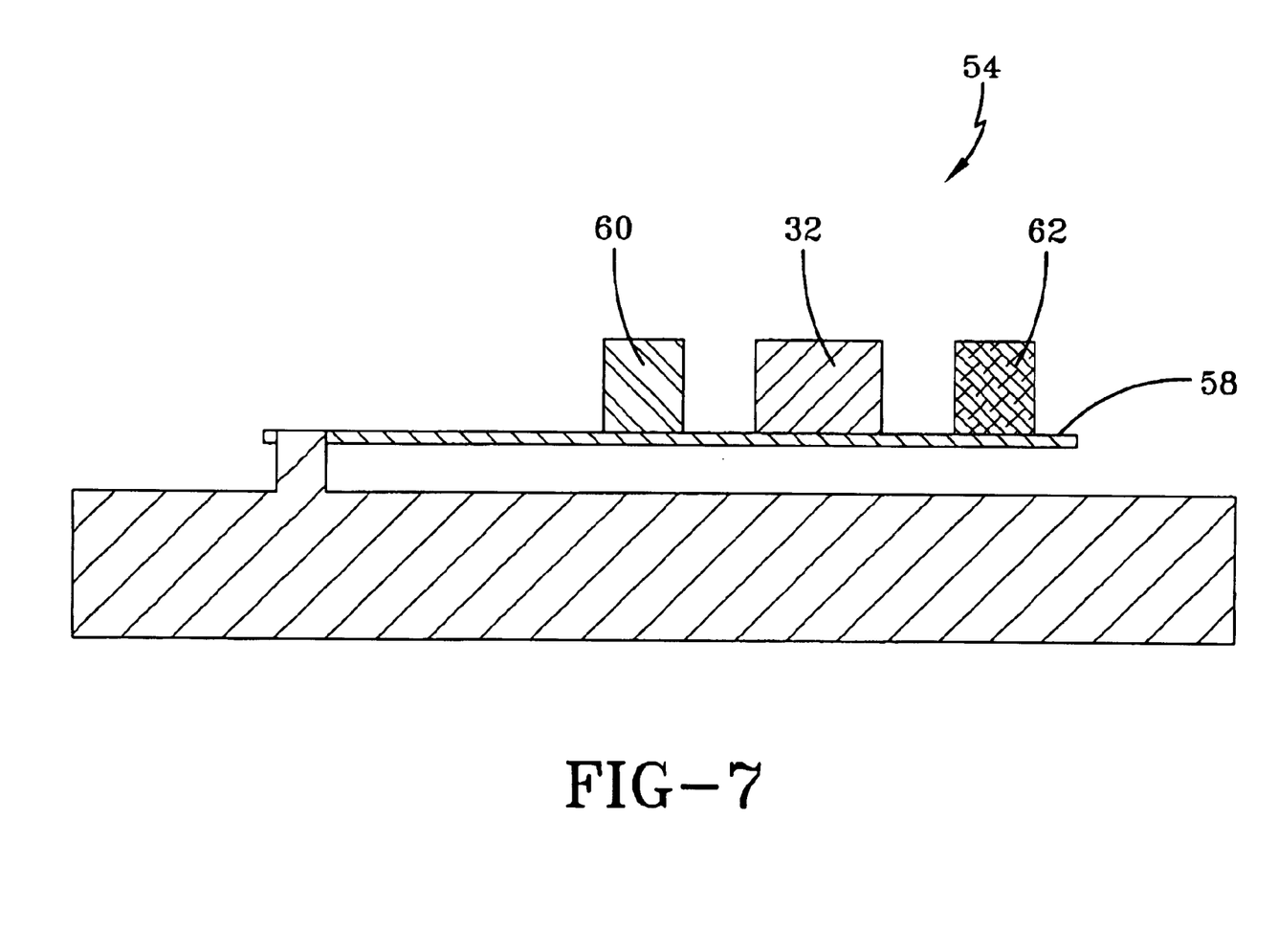
FIG. 7 is a further embodiment of a gas sensing device of the present invention that utilizes a SiC epilayer comprised of at least one thin lateral cantilever.

FIG. 7 illustrates that the gas sensing device 54 has a flat SiC epilayer that is comprised of at least one thin lateral cantilever 58, each having a typical thickness of a micrometer or a few micrometers. The atomically-flat cantilevers may be formed by the process described in U.S. Pat. No. 6,461,944, and herein incorporated by reference. In particular, the cantilever 58 is comprised of an atomically-flat epilayer as described in U.S. Pat. No. 6,461,944 and the technical article of Neudeck et al entitled "Enlargement of Step-Free SiC Surfaces by Homoepitaxial Web Growth of Thin SiC Cantilevers" published in Journal of Applied Physics, vol 92, no. 5, pp. 2391–2400, 2002. The gas sensing layer 32 is patterned to reside on the thin lateral epilayer cantilevers 58, as shown in FIG. 7. The gas sensing device 54 having the thin lateral cantilevers 58 serves to reduce the thermal mass thereof with benefits described in the previously mentioned technical article of Hunter et al in 2001. More particularly, the cantilevers 58 reduce the structure for the region occupied by SiC crystal which, in turn, advantageously reduces the thermal mass of the gas 54 sensing device. The gas sensing device 54 further comprises a temperature detector structure 60 and a heater structure 62 deposited on the SiC epilayer cantilevers 58, in a manner known in the art and as also described in the Hunter technical article.

Figure 8:
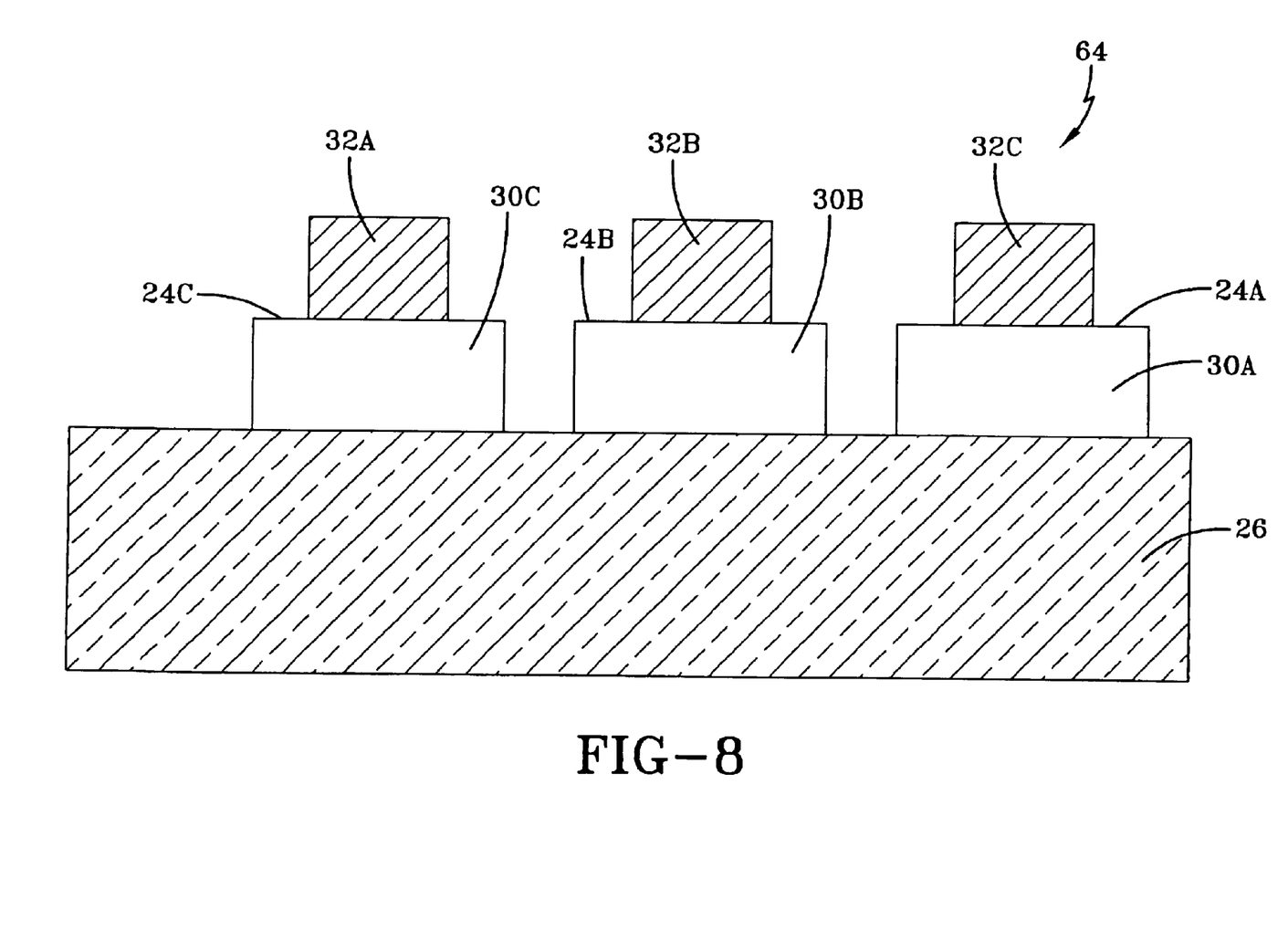
FIG. 8 is a still further embodiment of the present invention that is composed of multiple gas sensing devices on multiple atomically flat mesas.

FIG. 8 illustrates a further embodiment in a gas sensing device 64 that is similar to the gas sensing device 44 in FIG. 5, but in addition thereto comprises two additional arrangements of gas sensing layers 32 all of materials selected to sensors with sensitivity to various gases. In particular, gas sensing layer 32A of FIG. 8 may be selected to sense one selected gas of interest, while layer 32B may be selected to sense a different gas, while layer 32C might be selected to sense yet a third gas. In another embodiment, the gas sensing layers 32A, 32B, and/or 32C might be selected to provide signals for different concentration ranges of the same gas species. While FIG. 8 depicts an array of metal-semiconductor gas-sensing devices, the array of sensing devices could also be comprised of MESFET devices instead of Schottky diode devices, or combinations thereof. Similarly, the array could also be comprised of devices optimized for either capacitance sensing or current sensing, or combinations thereof. Regardless of the specific choice of the device array to sense a specific set of desired gases, the atomically flat interface of the present invention is expected to improve sensor performance as discussed previously.

Figure 9:
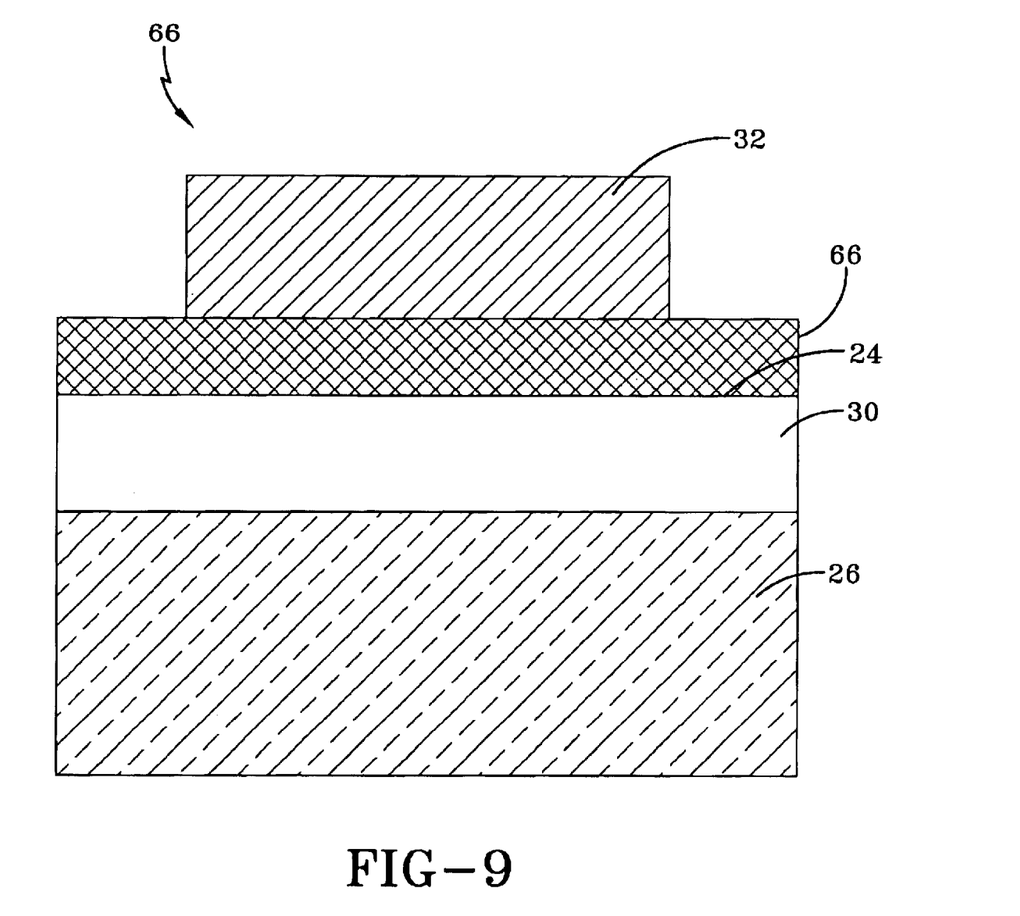
FIG. 9 is an additional embodiment of a gas sensing device of the present invention that utilizes an interface layer residing on top of an atomically flat single crystal silicon carbide epilayer.

A further gas sensing device 66 in accordance with another embodiment of the present invention is illustrated in FIG. 9. The gas sensing device 66 of FIG. 9 is quite similar to the gas sensing device 28 of FIG. 3, but in addition thereto, comprises an interface layer 66 residing on top of the atomically flat single crystal silicon carbide epilayer 30. The interface layer 66 is preferably an electrochemically active material with electrical properties that change in response to the presence of gas. The electrochemically active interface layer 66 may be of a material selected from the group comprising Sn,Ti,W,Ga,Zr,Ta,Sr and combinations, oxides, and alloys thereof, as well as $SrTiO_2$. The interface layer 66 may also preferably be at least partially comprised of a single crystal heteroepitaxial layer, wherein the material of the heteroepitaxial layer is selected from the group consisting of 3C—SiC, AlN,GaN,AlGaN, InN,InGaN,INAiN,AlInGaN, silicon, and diamond. The interface layer may also be electrochemically passive consisting of $SiO2,Si3N4$, chrome carbide, TiC,TiN,ZrB2, HfB2,MoO3,Al2O3,MoSi2, and combinations of these materials. For the arrangement shown in FIG. 9, the gas layer 32 may be of material selected from the group consisting of Pt, Pd, Au, Ir, Ag, Ru, Rh,In,Os,Cr,Ti, and alloys of these metals with each other.

Metal-oxide-semiconductor, known by acronym as MOS devices, have also been studied for use in gas sensor applications. The metal-oxide-semiconductor field effect transistor, commonly referred to by acronym as MOSFET, is a three terminal transistor device well known to those skilled in the art and has many similarities in structure and operation to the MESFET device discussed previously. A major difference between the previously discussed MESFET device structure and the MOSFET device structure is the presence of a gate insulator material, usually SiO2 (i.e., silicon dioxide), between the transistor gate electrode and the channel that conducts between the transistor source and drain terminals. When non-oxide materials are used to insulate the gate electrode from the channel, the device is also referred to as a metal-insulator-semiconductor field effect transistor, MISFET by acronym. When the interface layer 66 is selected to be sufficiently insulating, MOS/MIS devices, including the MOSFET, can be fabricated. The operation of a MISFET device as a gas sensor is described in the technical article "MISFET Chemical Sensors For Applications in Exhaust Gases and Fuel Gas" Proc. ECSCRM2002, LinÖkping Sep. 2–5, 2002, H. Wingbrant et al. However, when implemented in SiC, these devices all have the drawbacks of the stepped structure "off-axis" SiC insulator interfaces.

The present invention is directed toward eliminating the drawbacks of the conventional stepped SiC interface structure by providing an atomically flat semiconductor interface for beneficial use in gas sensors. Some of the general benefits of atomically flat surfaces/interfaces to MISFET devices, without respect to gas sensor devices, are described in the '194 specification.

Figure 10:
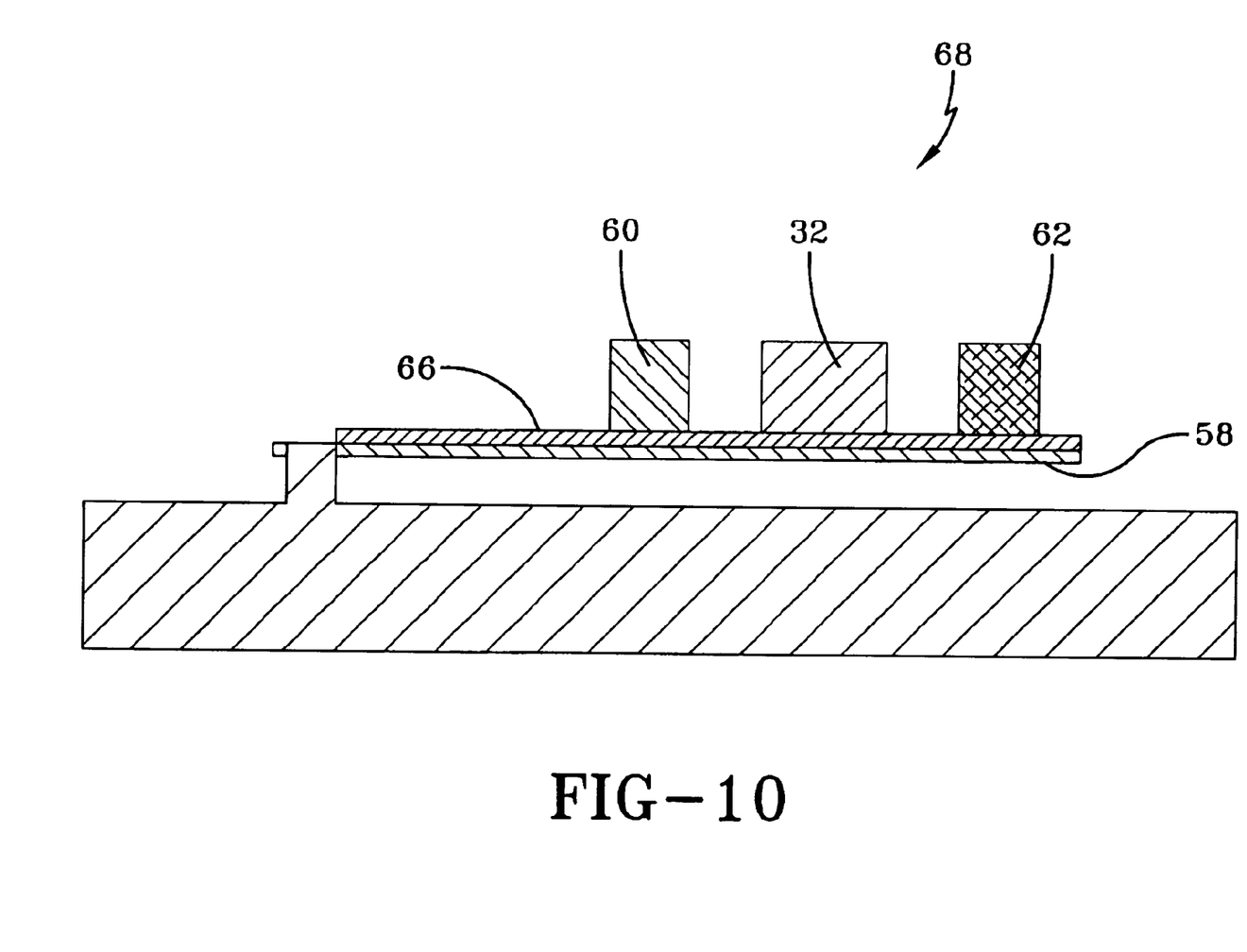
FIG. 10 is a still further embodiment of a gas sensing device of the present invention that utilizes an interface layer residing on top of a SiC epilayer comprised of at least one thin lateral cantilever.

FIG. 10 illustrates a further embodiment of a gas sensing device 68 that has some of the features of a gas sensing device 66 of FIG. 9 and a gas sensing device 54 of FIG. 7. More particularly, the gas sensing device 68 has the epilayer having the one or more thin cantilevers 58, previously described with reference to FIG. 7, but in addition thereto has the interface layer 66 residing on the epilayered cantilever 58. Further, the gas sensing device 68 includes the temperature detector 60 and the heater 62, previously described with reference to FIG. 7.

In another embodiment, the interface layer 66 is comprised of two layers, namely a heteroepitaxially grown single-crystal 3C—SiC layer residing below an SiO2 layer that is thermally grown or deposited on top of the 3C—SiC by processing known in the art. The heteroepitaxial growth of the 3C—SiC on top of the atomically flat 6H—SiC may be carried out in a manner described in U.S. Pat. No. 5,915,194 and 6,488,771 B1. In essence, this structure forms a 3C—SiC metal-oxide semiconductor (3C—SiC MOS) device, which could either be a gas-sensitive MOS diode or a gas-sensitive metal-oxide-semiconductor field-effect transistor (MOSFET). Experiments have shown 3C—SiC MOS devices to have some superior electrical interface properties than 4H—SiC and 6H—SiC MOS devices. Therefore, use of the 3C—SiC MOS structure as a two-component interface layer 66 could likewise offer superior MOS interface and therefore gas-sensing properties.

It should be still further appreciated that without the benefits of the present invention that provide atomically flat surfaces serving interfaces for SiC gas sensors, the standard SiC surface has sites of enhanced reactivity due to the formation of steps on the top surface. On a local scale, the step risers are surfaces of higher reactivity and basal plane terrace are surfaces of lesser reactivity. The present invention eliminates the disadvantageous higher reactivity of step risers. In addition, the formation of an interface layer provided by the present invention between the atomically flat SiC and the first layer of gas sensitive material not only defines, but reduces the reactivity of the sensor due to interface states, thereby improving the stability of the sensor.

It has been difficult to reproduce sensor stability, perhaps due to changes in semiconductor surface and lack of reproducibility of the interface layer. Reactive sites, without the benefits of the present invention, may either promote or degrade the formation of an interface layer. Thus, these reactive sites may, for example, produce holes in a thin interface layer, which can allow migration of material through the interface and cause the degradation of the sensor. All these drawbacks are eliminated by the present invention.

One of the advantages of the present invention is to produce a uniformly reactive surface without steps on which the sensing material can be placed. The atomically flat surface used by the present invention also means a more uniform film gas sensing or interface layer. This results in a more uniform sensor/semiconductor interface and potentially a more stable sensor. If the interface layer is thin or essentially non-existent, this uniform surface allows more uniform formation of reaction products, which might advantageously form natural barrier layers. For example, this uniform surface allows the growth of a more uniform and coherent oxide.

The present invention aids in determining the optimum gas sensor configuration, due to the fact that one is consistently dealing with a repeatable SiC surface for sensor deposition. If a given combination materials gave good sensor responses once, then one would expect more reproducible results since the atomically flat SiC starting surface is more reproducible.

The invention has been described with reference to preferred embodiments and alternates thereof. It is believed that many modifications and alterations to the embodiments as discussed herein will readily suggest themselves to those skilled in the art upon reading and understanding the detailed description of the invention. It is intended to include all such modifications and alterations insofar as they come within the scope of the present invention.

What we claim is:

1. A gas sensing device that produces a change in electrical signal due to the presence of a gas, wherein the gas sensing device is comprised of a gas sensing layer residing on top of a single crystal silicon carbide (SiC) epilayer having an atomically flat top surface.

2. The gas sensing device according to claim 1, wherein said SiC epilayer having said atomically flat top surface is formed on top of a mesa patterned on a SiC substrate.

3. The gas sensing device according to claim 2, wherein said SiC epilayer is a wedge-like epitaxial layer having non-uniform thickness, wherein the thickness of said epilayer is essentially zero at one location on said mesa.

4. The gas sensing device according to claim 3, wherein the said gas sensing layer is deposited and patterned to reside near the thickest part of said wedge-like epitaxial layer.

5. The gas sensing device according to claim 2 wherein said epilayer resides on a SiC substrate and, wherein said mesa is isolated from the surrounding SiC substrate by a depth of an etch used to form said mesa pattern thereby eliminating a need for passivation surrounding said gas sensing device.

6. The gas sensing device according to claim 1, wherein said gas sensing layer is selected from the group of materials consisting of Pt, Pd, Au, Ir, Ag, Ru, Rh, In, Os, Cr, Ti, and alloys of these metals with each other, and oxides of materials Sn Ti, W, Ga, Zr, and Ta, and $SrTiO_2$.

7. The gas sensing device according to claim 6, wherein said gas sensing layer of said gas sensing device is selected to be of one or more materials so as to provide a metal-semiconductor diode.

8. The gas sensing device according to claim 7, wherein the electrical signal response of said metal-semiconductor diode is determined by measuring the current flow of said diode at a selected applied bias.

9. The gas sensing device according to claim 7, wherein the electrical signal response of said metal-semiconductor is determined by measuring the capacitance of said diode at a selected applied bias.

10. The gas sensing device according to claim 7, wherein a protective layer comprising a filter made of high temperature material covers said metal-semiconductor diode.

11. The gas sensing device according to claim 6, wherein said gas sensing layer of said gas sensing device is selected to be of one or more materials so as to provide a metal-semiconductor field effect transistor having a drain electrode.

12. The gas sensing device according to claim 11, wherein the electrical signal response of the metal-semiconductor field effect transistor is determined by measuring the current flow of said metal-semiconductor field effect transistor at a selected applied bias.

13. The gas sensing device according to claim 12, wherein said current flow is measured at said drain electrode of said metal-semiconductor field effect transistor.

14. The gas sensing device according to claim 1, wherein said atomically flat SiC epilayer is comprised of at least one thin lateral cantilever, wherein at least some of said gas sensing layer is patterned so as to reside on said thin lateral cantilever.

15. The gas sensing device according to claim 14, wherein said thin lateral cantilever serves to reduce the thermal mass of a region of said gas sensing device, and wherein a temperature detector and heater are deposited on said region of reduced thermal mass.

16. The gas sensing device according to claim 1, wherein the gas sensing device as a whole is composed of multiple gas sensing devices on multiple atomically flat surfaces.

17. A gas sensing device that produces a change in electrical signal due to the presence of a gas, wherein the gas sensing device is comprised of a gas sensing layer residing on top of an interface layer residing on top of a single crystal silicon carbide (SiC) epilayer having an atomically flat surface.

18. The gas sensing device according to claim 17, wherein said gas sensing layer is selected from the group of materials consisting of Pt, Pd, Au, Ir, Ag, Ru, Rh, In, Os, Cr, Ti, and alloys of these metals with each other.

19. The gas sensing device according to claim 17, wherein said interface layer is an electrochemically passive material.

20. The gas sensing device according to claim 19, wherein said electrochemically passive interface layer is of a material selected from the group consisting of SiO2, Si3N4, chrome carbide, TiC, TiN, ZrB2, HfB2, MoO3, Al2O3, MoSi2, and combinations of these materials.

21. The gas sensing device according to claim 17, wherein said interface layer is an electrochemically active material with electrical properties that change in response to the presence of gas.

22. The gas sensing device according to claim 21, wherein said electrochemically active interface layer is comprised of oxides of materials selected from the group comprising Sn, Ti, W, Ga, Zr, Ta, Sr, and combinations thereof, as well as $SrTiO_2$.

23. The gas sensing device according to claim 17, wherein said interface layer is at least partially comprised of a single crystal heteroepitaxial layer, wherein said heteroepitaxial layer is a material selected from the group consisting of 3C—SiC, AlN, GaN, AlGaN, InN, InGaN, InAlN, AlInGaN, silicon, and diamond.

24. The gas sensing device according to claim 23, wherein said interface layer is comprised of SiO2 on top of a single crystal 3C—SiC heteroepitaxial layer.

25. The gas sensing device according to claim 24, wherein said gas sensing device is a metal-semiconductor field effect transistor.

26. The gas sensing device according to claim 17, wherein said gas sensing device is selected so as to provide a device selected from the group consisting of a capacitor, a metal-oxide-field-effect transistor, and a Schottky diode.

27. The gas sensing device according to claim 26, wherein said selected device has a structure that includes a said gas sensing layer that is selected from the group consisting of Pt, Pd, Au, Ir, Ag, Ru, Rh, In, Os, Cr, Ti, and alloys of these metals with each other, and wherein said interface layer is selected from the group consisting of SiO2, Si3N4, chrome carbide, TiC, TiN, ZrB2, HfB2, MoO3, Al2O3, MoSi2, and combinations of these materials.

28. The gas sensing device according to claim 26, wherein a protective layer comprising a filter made of high temperature material that covers the said device is selected from the group consisting of a capacitor, a metal-oxide field effect transistor, and a Schottky diode.

29. The gas sensing device according to claim 17 wherein said SiC epilayer resides on a SiC substrate and, wherein said SiC epilayer is formed on a mesa pattern etched on a SiC substrate.

30. The gas sensing device according to claim 29, wherein said mesa is isolated from the surrounding SiC substrate by a depth of said mesa pattern etch thereby eliminating a need for passivation surrounding the gas sensing device.

31. The gas sensing device according to claim 17, wherein said atomically flat SiC epilayer is comprised of at least one thin lateral cantilever, wherein at least some of said gas sensing layer is patterned to reside on said thin lateral cantilever.

32. A gas sensing device according to claim 31, wherein said lateral cantilever serves to reduce the thermal mass of a region of said gas sensing device, and wherein a temperature detector and heater are deposited on said region of reduced thermal mass.

33. The gas sensing device according to claim 17, wherein said gas sensing device is composed of a plurality of gas sensing devices.

* * * * *